United States Patent [19]

Endo

[11] Patent Number: 4,955,867

[45] Date of Patent: Sep. 11, 1990

[54] PERITONEAL DIALYSIS CATHETER PROTECTOR BELT

[76] Inventor: Walter Y. Endo, 3515 S. Wellington Rd., Los Angeles, Calif. 90016

[21] Appl. No.: 350,774

[22] Filed: May 12, 1989

[51] Int. Cl.⁵ ............................................. A61M 5/32
[52] U.S. Cl. ..................................................... 604/179
[58] Field of Search ............................. 604/179, 174

[56] References Cited

U.S. PATENT DOCUMENTS 4,582,508  4/1986  Pavelka ............................... 604/179
4,596,560  6/1986  Simpson .............................. 604/174
4,738,661  4/1988  Marut ................................. 604/179

Primary Examiner—John D. Yasko

[57] ABSTRACT

A fabric or paper belt or band, which may be disposable, and which is adapted to be fastened around the abdomen of a patient adjacent to the protruding end of a peritoneal dialysis catheter. The belt is equipped with an open-ended pouch into which the end of the catheter may be inserted and which serves completely to enclose and protect the end of the catheter and to prevent it from dangling.

6 Claims, 1 Drawing Sheet

PERITONEAL DIALYSIS CATHETER PROTECTOR BELT

BACKGROUND OF THE INVENTION

The invention provides a belt or and to be worn around the waist of the patient and over the abdomen, the belt being equipped with a pouch for receiving the protruding end of a peritoneal dialysis catheter when the catheter is not in use.

In hemodialysis, the patient's blood is circulated and cleansed outside the body. The blood is withdrawn through a needle inserted in a blood vessel in the patient's arm or leg. The needle is attached by plastic tubing to a hemodialysis machine. The machine pumps the patient's blood out of the body and through a dialyzer containing a synthetic semipermeable membrane. The hemodialysis machine keeps the blood moving through the dialyzer while wastes and fluid are being filtered out. It then returns the cleansed blood to the patient through a second needle in the same blood vessel. Patients who need long term hemodialysis treatment are connected to a dialysis machine for four to six hours at a time, two or three times a week.

In contrast to hemodialysis, peritoneal dialysis works inside the body using the body's own peritoneal membrane as the semipermeable barrier through which the blood can be filtered The peritoneal membrane lines the peritoneal or abdominal cavity and covers the organs that fit into it, such as the stomach, liver, spleen and intestines.

During the peritoneal dialysis procedure, a tube called a catheter is inserted through the wall of the abdominal cavity. This provides an opening through which dialysis solution can be instilled into the abdominal cavity. The cavity can then be used as a reservoir for the dialysis solution. Waste products pass from the blood stream, through the peritoneal membrane, and into the dialysis solution. The used dialysis solution is periodically drained from the abdominal cavity and replaced with fresh solution.

It is usual for a patient undergoing peritoneal dialysis for the protruding end of the catheter to dangle loosely from the abdomen when not in use. However, this can cause the catheter to be irritating to the patient, to become tangled in the patient's clothes, and to cause unsightly bulges.

Moreover, there is a danger that the dangling catheter may become caught in furniture or other objects which could result in painful consequences and internal bleeding.

The present invention provides a simple means for receiving and retaining the protruding end of the peritoneal dialysis catheter. As explained briefly above, this means takes the form of a fabric or paper belt or band, which may be disposable, and which is fastened around the abdomen of the wearer. The belt is equipped with an open-ended pouch, into which the dangling end of the catheter may be inserted, and which serves completely to enclose and protect the end of the catheter.

DETAILED DESCRIPTION OF THE ILLUSTRATED EMBODIMENT

Figure 1:
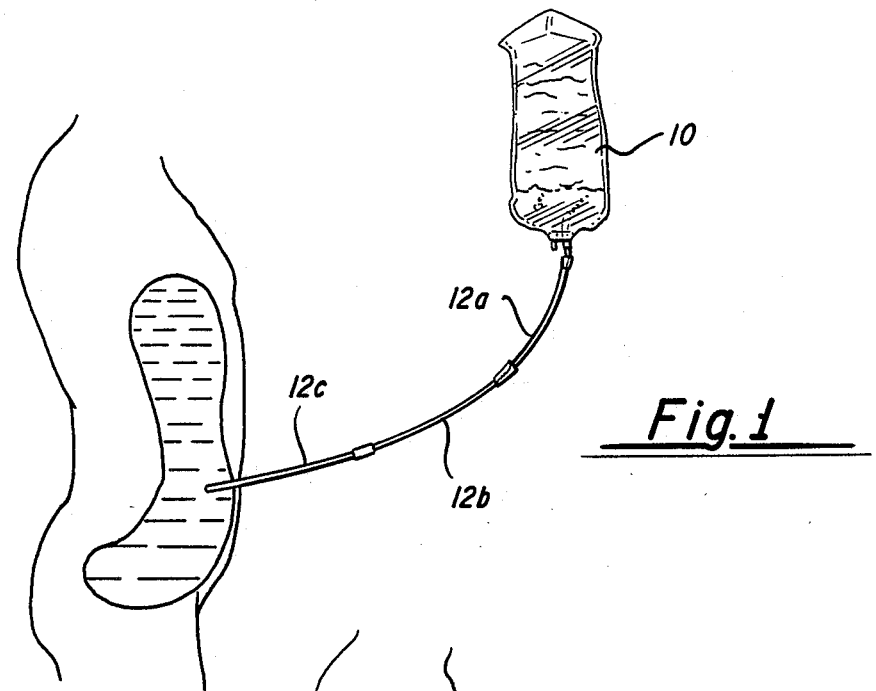
FIG. 1 is a schematic representation showing how the dialysis solution is instilled in the abdominal cavity during the peritoneal dialysis procedure.

As illustrated in FIG. 1, peritoneal dialysis works inside the body. During the procedure, the dialysis solution flows from a collapsible bag 10 through a series of catheter tubes 12a, 12b and 12c into the abdominal cavity of the patient where it collects waste products from the blood.

Figure 2:
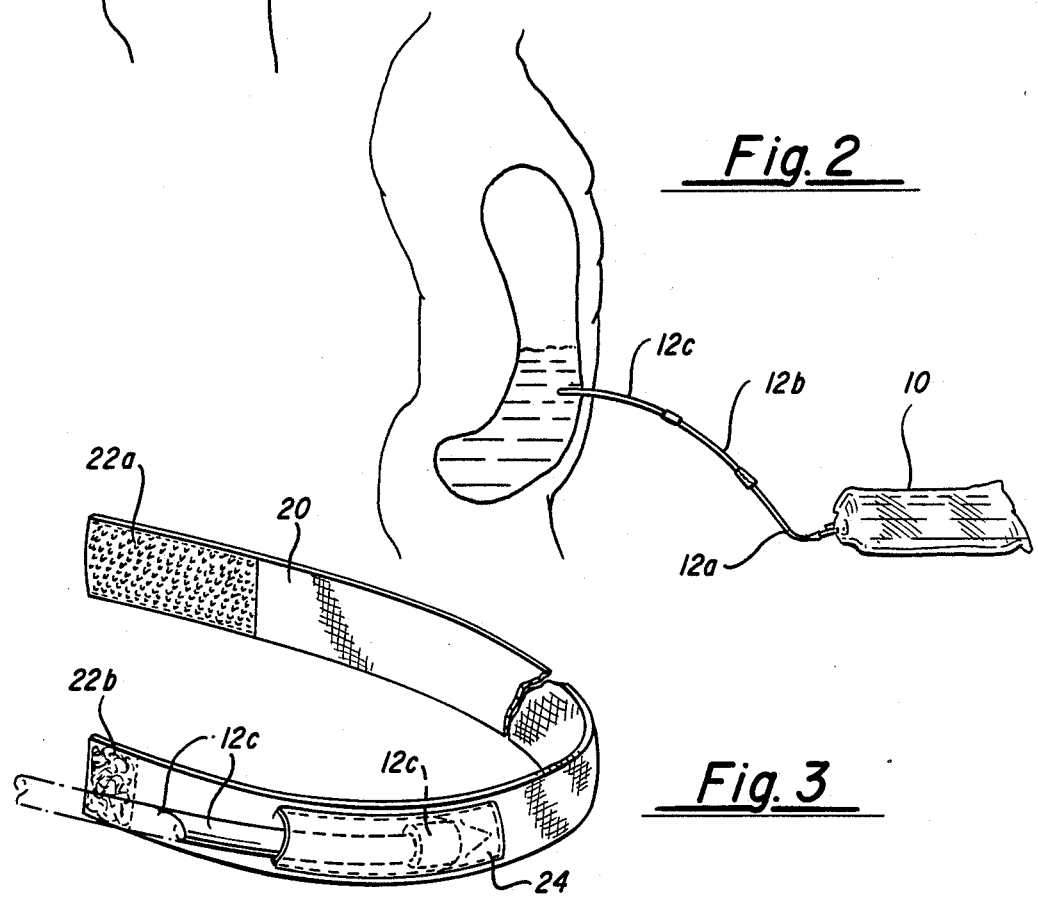
FIG. 2 is a schematic diagram showing how the dialysis solution is periodically drained from the abdominal cavity.

As shown in FIG. 2, periodically the used dialysis solution is drained from the abdominal cavity back to bag 10 through the catheter tubes 12c, 12b and 12a, carrying away waste products and excess water from the blood.

When the procedure is not taking place, the bag 10, and catheters tubes 12a and 12b are detached from the catheter tube 12c. The catheter tube 12c is then clamped and capped.

However, as mentioned above, it has been the usual practice between procedures to permit the protruding end of the catheter tube 12c to dangle from the patient which, as noted, can lead to undesirable results.

Figure 3:
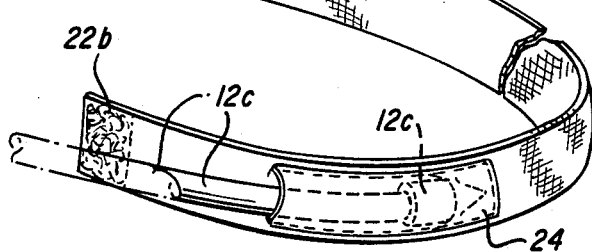
FIG. 3 is a perspective representation of a belt or band constructed in accordance with the concepts of the present invention.

In accordance with the present invention, a belt 20 (FIG. 3) is provided which may be placed around the waist of the patient and fastened by Velcro fasteners 22a and 22b at the ends of the belt. The belt is fastened around the patient to be displaced slightly from the protruding end of the catheter 12c. An open-ended pouch 24 is fastened to the belt 20. The protruding end of catheter 12c may be inserted into the pouch 24 through its open end and snugly held by and retained in the pouch.

The belt 20 may be formed, for example, of fabric or paper, as mentioned above, and it may be disposable. The pouch 24 may be mounted on the belt 20 for right-handed or left-handed use, as is desired by the patient.

The invention provides, therefore, a convenient means for retaining and housing the protruding end of a peritoneal dialysis catheter, so as to overcome the inconveniences and other disadvantages of merely permitting the end of the catheter to dangle from the patient.

It will be appreciated that while a particular embodiment of the invention has been shown and described, modifications may be made. It is intended in the claims to cover all modifications which come within the spirit and scope of the invention.

I claim:

1. A article for retaining and protecting the protruding end of a peritoneal dialysis catheter comprising: a flexible belt adapted to extend around the waist of a patient having the end of a peritoneal dialysis catheter protruding from the abdomen, the belt being adapted to be positioned on the abdomen adjacent to the protruding end of the catheter, said belt having an inner side and an outer side; and a pouch affixed to the outer side of the belt and extending longitudinally along the belt, said pouch having an open end for receiving the protruding end of the catheter, and said pouch having a closed end, said pouch serving to retain the end of the catheter within the pouch.

2. The article defined in claim 1, and which includes fastening means affixed to the ends of the belt.

3. The article defined in claim 2, in which said fastening means comprises a Velcro fastener.

4. The article defined in claim 1, in which said belt and pouch are formed of a flexible fabric material.

5. The article defined in claim 1, in which said belt and said pouch are formed of paper.

6. The article defined in claim 1, in which said belt and pouch are disposable.

* * * * *